(12) United States Patent
Lurie et al.

(10) Patent No.: US 8,755,902 B2
(45) Date of Patent: Jun. 17, 2014

(54) SYSTEMS AND METHODS FOR PLACING ELECTRONIC DEVICES INTO "CAUTERY-SAFE" MODE

(75) Inventors: Keith Lurie, Minneapolis, MN (US); Barbara S. Gold, Minneapolis, MN (US); David Benditt, Edina, MN (US); Andres Belalcazar, Roseville, MN (US)

(73) Assignee: ResQCor, Roseville, MN (US)

( * ) Notice: Subject to any disclaimer, the term of this patent is extended or adjusted under 35 U.S.C. 154(b) by 582 days.

(21) Appl. No.: 12/793,374

(22) Filed: Jun. 3, 2010

(65) Prior Publication Data

US 2011/0160782 A1   Jun. 30, 2011

Related U.S. Application Data

(60) Provisional application No. 61/291,211, filed on Dec. 30, 2009, provisional application No. 61/296,391, filed on Jan. 19, 2010.

(51) Int. Cl.
*A61N 1/37* (2006.01)

(52) U.S. Cl.
USPC .......................................................... 607/63

(58) Field of Classification Search
USPC .............................................. 607/59, 60, 63
See application file for complete search history.

(56) References Cited

U.S. PATENT DOCUMENTS

| | | | | |
|---|---|---|---|---|
| 5,197,468 A * | 3/1993 | Proctor et al. | ..................... | 607/9 |
| 6,044,301 A * | 3/2000 | Hartlaub et al. | ................. | 607/31 |
| 2002/0095190 A1 * | 7/2002 | Bornzin et al. | ................. | 607/28 |
| 2004/0230275 A1 * | 11/2004 | Marshall et al. | .............. | 607/122 |
| 2011/0093040 A1 * | 4/2011 | Ellingson et al. | ............... | 607/59 |

OTHER PUBLICATIONS

Suresh, et al., "Suppression of Cautery-Induced Electromagnetic Interference of Cardiac Implantable Electrical Devices by Closely Spaced Bipolar Sensing," *Anesthesia & Analgesia*, vol. 112, No. 6, Jun. 2011, pp. 1358-1361.

* cited by examiner

*Primary Examiner* — Carl H Layno
*Assistant Examiner* — Paula J Stice
(74) *Attorney, Agent, or Firm* — Kilpatrick Townsend & Stockton LLP

(57) ABSTRACT

A method and device to enable a medical or surgical procedure using electro-cautery on a patient with an implantable device in a cautery-safe mode of operation. In one embodiment, the invention provides an electronic implantable device programmer having a computer processor, and a display screen configured to display information based on signals from the computer processor. The programmer also includes an input device, and a wireless transmitter controlled by the computer processor. The programmer display and input give the operator the option of programming an implanted electronic device in a cautery-safe mode. With this input, from the operator, instructions are provided in the programmer to transmit a signal from the wireless transmission device to the implanted electronic device to program the electronic device to be in a dedicated bipolar mode where electrical noise produced when operating an electro-cautery device during and medical/surgical procedure does not interfere with operation of the electronic device.

10 Claims, 8 Drawing Sheets

SYSTEMS AND METHODS FOR PLACING ELECTRONIC DEVICES INTO "CAUTERY-SAFE" MODE

CROSS REFERENCES TO RELATED APPLICATIONS

This application is a non-provisional application and claims the benefit of U.S. Provisional Application No. 61/291,211, filed Dec. 30, 2009, and U.S. Provisional Application No. 61/296,391, filed Jan. 19, 2010, the complete disclosures of which are herein incorporated by reference.

BACKGROUND OF THE INVENTION

Electro-cautery, also referred to simply as "cautery" or "electric cautery" is commonly used in the surgical operating room (OR), and other medical/surgical procedure sites, for a wide variety of applications, including cutting through tissue with minimal bleeding and hemostasis or the termination of bleeding. It is used during a wide range of medical/surgical procedures, from brain surgery and eye surgery, to open heart and colorectal surgery. Electro-cautery is typically delivered in the unipolar or bipolar mode. It is often used in patients who already have an implantable therapeutic devices or monitoring devices that operate electrically, such as cardiac pacemakers, implantable cardiac defibrillators (ICD), neurological stimulators, gastric stimulators, electrocardiographic [ECG] monitors, physiologic sensor systems and similar devices. Cautery is also used during the implantation for other medical/surgical procedures in patients who already have implantable devices (e.g., pacemakers, ICDs) in place. At present, there is concern that use of cautery, especially unipolar cautery, has the potential to interfere with normal implantable pacemaker and implantable cardioverter defibrillator (ICD) function. Specifically, there are concerns that the pacemaker may sense the electrical 'noise' (i.e., electrical signals) generated by the cautery device and this sensing of these extraneously generated electrical signals will either inhibit pacemaker/ICD function or potentially cause a change in pacemaker/ICD programming, or damage implantable device circuitry.

At the present time, conventional medical/surgical practice is such that during surgery of any form (whether placement of the implantable therapeutic device itself, or concomitant surgery in an individual who has an implantable device that was placed previously), there is the potential for electrical interference with an implantable pacemaker or defibrillator and the concern is further heightened if the cautery is performed within 6 inches of the implantable device. As such, it is recommended by many manufacturers and medical specialty organizations that write clinical guidelines that patients with pacemakers or ICDs undergo device reprogramming prior to surgery to preclude the implantable device from detecting the external electrical signal and thereby avoid altering implantable device function. Such pre-surgical intentional reprogramming may include disabling therapeutic or sensing functions of the implanted pacemaker or ICD device, leaving the patient temporarily without the defibrillation or pacing benefits of the implanted device. Furthermore, given the recommendation to pre-operatively reprogram devices to a non-sensing mode, additional recommendations are given by implantable device manufacturers and medical specialty organizations that write clinical guidelines that these implanted therapeutic or monitoring devices need to be re-assessed after surgery, at which time they are reprogrammed back to the pre-surgical normal function. These programming and re-programming steps require considerable human resources, and may be inconvenient in emergency situations as well as during procedures in which manufacturer representatives or specialized implantable device professionals are not typically present.

BRIEF SUMMARY OF THE INVENTION

In certain embodiments, the invention provides implantable electronic devices, such as pacemakers or ICDs, that can be easily programmed to a "cautery-safe" mode prior to the surgery, or can be programmed by a single or simple device programming step, including by individuals who are not generally implantable device experts (e.g. emergency room physicians, preoperative nurses, OR technicians, etc). Such a function simplifies both elective and urgent management of patients undergoing surgical procedures in which cautery may be used without the need to worry on the day of surgery if the device is going to function as intended. After the procedure, a similar single or simple programming step returns the implanted electronic device to its pre-surgical programming state. Alternatively, a pre-set clock or other pre-determined mechanism may be used to reset the programming to the pre-operative setting for that individual patient baseline without further human interaction. In some cases, the implantable electronic device can be programmed at the time of implant or thereafter to a 'cautery-safe' mode and left in that mode indefinitely. One important aspect of this invention is the discovery that implantable cardioverter defibrillators that have previously been programmed to the dedicated bipolar configuration for routine functionality are in fact cautery-safe.

In one embodiment, the invention provides a method for programming an implantable device that was previously implanted into a patient. According to a method, the display screen of a computer is employed to display an option of programming the implantable electronic device in a cautery-safe mode (e.g., a 'button' on the computer screen that when activated results in initiation of the cautery-safe mode). After receiving a selection to place the electronic device in the cautery-safe mode, the computer transmits a signal to the implanted electronic device to program it to be in a dedicated bipolar mode. The dedicated bipolar mode is less much less susceptible to interference from extraneous electrical activity and consequently electrical noise produced when operating an electrocautery device does not interfere with operation of the electronic device. In this way, a healthcare provider can easily place the implanted electronic device into a cautery-safe mode prior to a surgical procedure, without requiring trained personnel to reprogram the implantable device on a separate visit prior to the date of operation.

In one aspect, the dedicated bipolar mode is a configuration where the sensing electrodes of an electrode pair are within less than about 10 mm to about 15 mm of each other. The method may be used with a wide variety of electronic devices, such as pacemakers, implantable cardioverter defibrillators (ICDs), neurological stimulators, gastric stimulators, ECG monitors, physiologic sensor systems, and the like.

In another aspect, a printer is employed to print a confirmation that the electronic device is programmed to the cautery-safe mode. In this way, the patient may provide evidence of the status of his or her implanted electronic device at the time of surgery. This may be useful if the intentional reprogramming is carried out hours or days prior to planned surgery in order to maximize efficiency of patient care on the day of surgery.

In another aspect, the healthcare provider may enter a time for the implanted electronic device to return to its normal operating mode. For example, the electronic device could be returned to a setting where ventricular sensing is in an integrated bipolar sensing mode. In this way, the implantable device may automatically return to normal operating mode following a procedure.

In another embodiment, the invention provides a programming device that comprises a computer processor and a display screen that is configured to display information based on signals from the computer processor. The device also includes an input device and a wireless transmitter controlled by the computer processor. The device further includes instructions to provide on the display screen a display giving the user the option of programming an implanted electronic device in a cautery-safe mode. The computer may also receive an input from the input device to place the electronic device in the cautery-safe mode. Based on this input, the wireless transmission device may transmit a signal to the implanted electronic device to program it to be in a dedicated bipolar mode where electrical noise produced when operating an electrocautery device, such as a unipolar or bipolar cautery device, does not interfere with operation of the implanted electronic device.

A device is considered to be in the dedicated bipolar mode when the sensing electrodes of an electrode pair are within less than about 15 mm of each other. In one implementation, the electronic device is a type of pulse generator, such as a pacemaker or ICD. The sensing electrodes are typically part of the lead that is attached to a pulse generator. The computer processor may further be configured to display a confirmation that the electronic device is currently in a cautery-safe mode. Also, a printer may be provided to print a confirmation that the device is programmed to the cautery-safe mode. Still further, when placing the implantable device into a cautery-safe mode, instructions may be wirelessly transmitted to return the electronic device to a normal operating device after a certain time period has elapsed. This option permits the cautery-safe mode to be programmed hours or days in advance of a planned procedure, and automatically revert to usual pre-operative programming after the procedure.

The invention further includes an implantable electronic device that is constructed of a housing, a processor, and a pulse-generating device disposed within the housing. Extending from the housing is a lead containing at least three electrical conductors, with at least two of these conductors coupled to ventricular sensing electrodes. The processor is configured to receive sensed signals via a sense amplifier from at least some of the electrodes and may include a pulse generator to apply electric energy to the electrodes to stimulate the heart. The processor is also programmable to a cautery-safe mode such that electrocautery can be used during a surgical procedure without electrical interference. In the cautery-safe mode, the ventricular sensing electrodes are placed in a dedicated bipolar sensing configuration. Typically, in such configuration the ventricular sensing electrodes are spaced apart by less than about 10 to about 15 mm, and the processor may be configured to return the electrodes to a normal operating mode after the passage of a certain period of time. In some cases the ventricular sensing electrodes may already be programmed to a dedicated bipolar configuration and in such circumstances programming or reprogramming to 'cautery-safe' mode provides a means to notify, or allow those performing the medical/surgical procedure to know, that it is safe to proceed with electro-cautery in that particular patient.

While certain embodiments employ the use of a desktop size computer with a display screen or monitor, some embodiments are configured to be handheld. For example, in one embodiment a handheld programming device comprises a housing that is sized to be handheld. A computer processor is held within the housing, and a wireless communication device is coupled to the processor. At least one button may be actuated to send a signal to the processor. When the button is pressed, the wireless transmitter transmits a wireless signal to an implantable device to reprogram the implantable device. The instructions may place the implantable device into a cautery-safe mode by switching electrodes of the implantable device to a dedicated bipolar mode. Alternatively, the implantable device may comprise an ICD that is placed into cautery-safe mode by disabling an anti-tachyarrhythmia therapy configuration of the ICD. In yet another alternative, the implantable device may comprise a pacemaker that is placed into cautery-safe mode by effecting asynchronous pacing for the pacemaker. As with the other devices, instructions may be used to return the implantable device to a normal operating mode after the passage of a certain period of time.

DETAILED DESCRIPTION OF THE INVENTION

Figure 1:
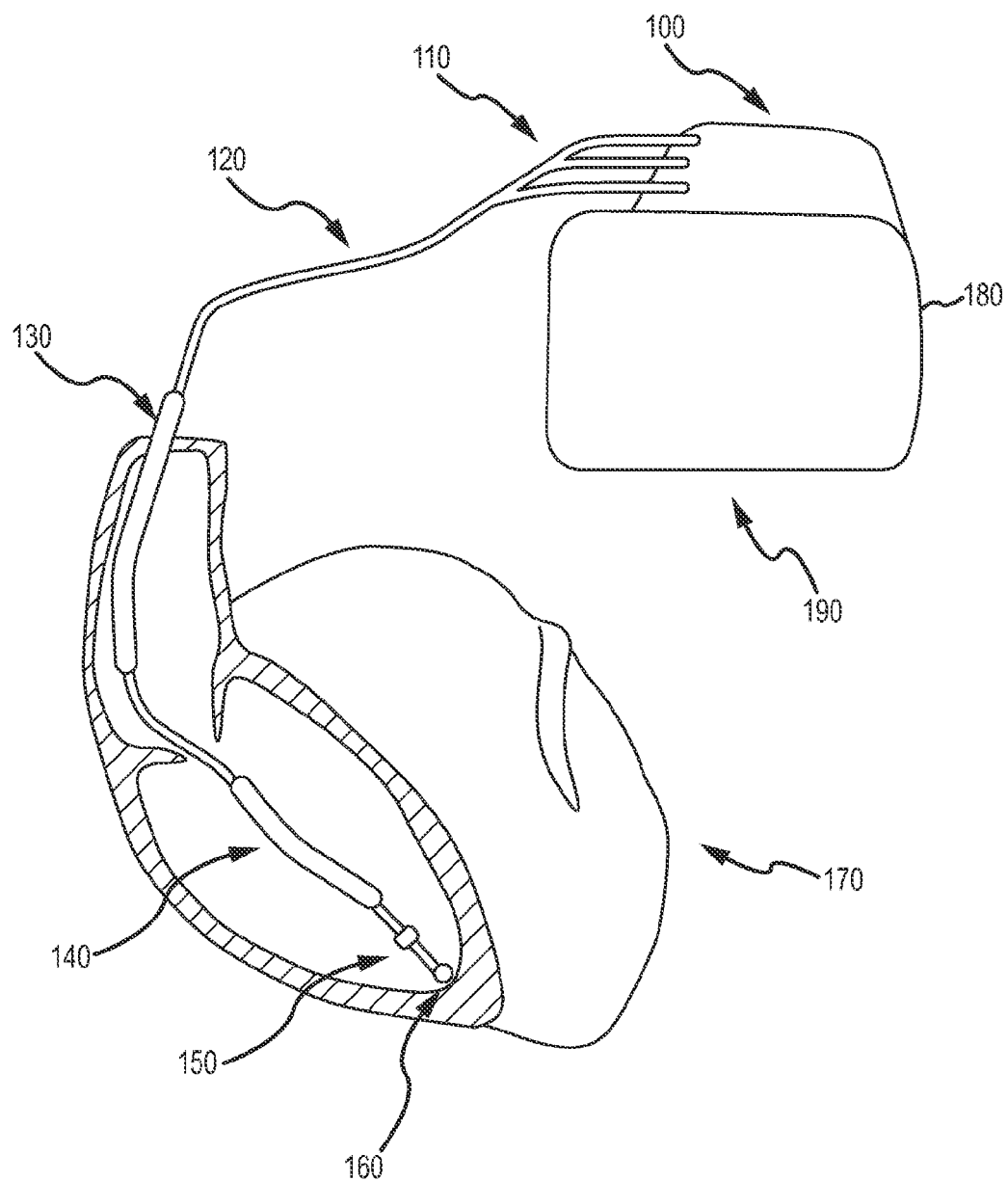
FIG. 1 illustrates one embodiment of an implantable device having a right ventricular lead, with the right side of the heart being shown cut away according to the invention.

Certain aspects of the invention describe a "cautery-safe" mode of an implantable electronic device that eliminates or greatly simplifies the need for reprogramming of the implantable electronic device prior to a surgical procedure for purposes of diminishing risk of essential device operation being affected adversely by electrical signals generated by electrocautery. The implantable electronic device may comprise a device with sensing and/or therapeutic capabilities, including pulse generators, such as pacemakers or ICDs. The cautery-safe mode can also be applicable to a wide range of other implantable electronic devices, such as neurological stimulators, gastric stimulators, ECG monitors, physiologic sensor systems and the like.

The cautery-safe mode is used to modify sensing and/or therapeutic functions of the implantable electronic device that may otherwise be interfered with when using cautery. For example, embodiments of the invention eliminate the need for ICD patients to have their tachycardia therapy turned off, e.g., when sensing remains on but therapy is inhibited, also known as "monitor only" mode. For pacemaker dependent patients, certain embodiments of the invention eliminate the need to have their pacing reprogrammed to ignore sensing, e.g., when they are reprogrammed to asynchronous pacing at a fixed pacing rate. For many implantable electronic devices, such as pacemakers, the cautery-safe mode still enables cardiac sensing, but does so in a way that operation of a conventional surgical electrocautery device during surgery is less likely to or will not interfere with operation of the pacemaker (or other implanted device). One advantage is that the invention could be used by medical professionals who are not typically experts in the management of implanted device to permit cautery use in urgent situations and not be obliged to wait for a trained professional device management individual or device company representative to arrive and reprogram the implanted device. Another advantage is that the invention could allow for the permanent programming of an implanted device to a cautery-safe mode so that the patient could undergo one or more surgical procedures at any time without concerns about interference from electro-cautery.

The cautery-safe mode can be achieved in a variety of ways. For example, it could be part of the software that controls the implantable device. This software can reside in the implantable device itself and/or in the external programmer that may include an interface that permits medical personnel to control operation of the implantable device. The programmer in one aspect of the invention could include a cautery-safe mode option as part of its standard menu interface. Selecting the cautery-safe mode causes a reprogramming of the implantable device so that it will switch to use sensing electrodes that reduce the cautery interference, while maintaining the therapeutic functions of the device. This improves not only the ease of use, but more importantly it preserves therapy functions in the period surrounding the surgery. In contrast, conventional devices have their therapies or sensing disabled prior to surgery. Selecting the cautery-safe "ON" button might be followed by a display query requiring reconfirmation that the cautery-safe selection was indeed desired. In this way, the reconfirmation step serves as a safety confirmation query.

In another aspect of the invention, a hand held, small programmer is provided having a simplified user interface (e.g., one or two buttons, and a few lights) and software and hardware to reprogram the implanted device, as described above. The advantage of a hand-held system is that it would be simple for non-implanted device experts to use, and inexpensive enough to be made available in clinics and emergency departments.

Yet another variation is to use a hand held programmer to inhibit therapies or sensing without switching electrodes. For example, for ICDs, the tachycardia therapy may be turned off, e.g., switched to "monitor only" mode, or for pacemakers the pacing may be reprogrammed to ignore sensing and placed, for instance, to asynchronous pacing at a fixed pacing rate. In such cases, the hand held device contains a simple interface with a dedicated function that allows the implantable electronic device to be programmed to a cautery-safe mode, without the need of a specially trained person who knows how to operate the traditional large, complex programmers. This embodiment t may be particularly useful for implantable devices that cannot be programmed to a dedicated bipolar mode. In another embodiment, such a handheld device may have software capable to identify implantable devices made by different manufacturers and thus be used to program a wide range of implantable devices manufactured by different manufacturers into and out of a cautery-safe mode.

In each of the embodiments described above, the implantable defibrillators and pacemakers may be programmed well in advance of a planned surgery, for example at a month checkup prior to surgery by medical professionals who are not typically implanted device experts. Similarly, the invention permits cautery use in urgent situations, where specialized personnel may not be readily available.

Embodiments of the invention include systems and methods for accomplishing the placement of an implantable electronic device into cautery safe mode, including the hardware and software for both computers that are used to remotely program pacemakers and defibrillators, as well as the implantable pacemakers and implantable defibrillators themselves, including their lead(s) systems and configurations. The term "cautery-safe" is meant to imply "operating room safe", electrocautery-safe, surgically-safe, procedure-safe, and the like terms. Also, the programmers, computers, handheld devices described herein may take advantage of various user interfaces. Such user interfaces may include a screen display with input devices (mice, wands, or the like), or simple buttons and lights with no screen displays.

Hence, techniques for placing an implantable device into cautery-safe mode include the use of a computer with a display screen, or a smaller hand held device, that permits the electrode configuration to be switched to a true (dedicated) bipolar mode. A hand held device could also be used to inhibit all therapy or to switch to asynchronous pacing without switching the electrode configuration. In all such cases, the implantable device can be configured to automatically return to its normal operating mode after the passage of a certain period of time. This could be, for example, one or two days. In this way, following surgery, the patient will not be required to return in order to reprogram the implantable device.

Certain aspects of the invention are based upon findings discovered during the implantation of ICDs in patients. In one case, electro-cautery was delivered to prevent bleeding in the pacemaker incision pocket at the time the ICD was implanted. Electrograms from the skin surface (ECG) and cardiac electrograms from the pacer leads were recorded before and after cautery. When the ICD was programmed such that the ventricular sensing was in the 'dedicated bipolar' configuration, there was no interference from the electro-cautery when it was delivered within <1 cm from the actual ICD generator. In the dedicated bipolar configuration, the sensing electrodes are closely spaced together, typically within about 1 cm center to center, and this reduces interference from noise sources away from the electrode pair.

By contrast, when the ICD was programmed such that the ventricular sensing was in the 'integrated bipolar' configuration, there was always interference from the electro-cautery when it was delivered within <1 cm from the actual ICD generator. In the integrated bipolar configuration, sensing of cardiac activity is measured between the tip and distal coil electrodes of the right ventricular lead, which are typically spaced apart by about 4 cm, center to center.

Hence, when the ICD was not programmed in the 'dedicated bipolar' (also known as 'true bipolar') configuration, cautery was incorrectly sensed by the ICD as ventricular fibrillation, and pacing was inhibited. However, when programmed to the dedicated bipolar mode, true ventricular fibrillation could be sensed, but interference from cautery was not, thus permitting the ICD to function as intended. This methodology will also reduce potential for interference by electro-cautery even when the surgery is close to the heart where the bipolar electrodes reside.

These observations were made in 20 patients undergoing placement of an ICD, when comparing the two different right ventricular electrogram sensing configurations ('dedicated bipolar' vs. integrated bipolar'). The reason for this unexpected observation lies in the fact that when the heart's electrical activity is sensed with a sensing electrode pair that is closely spaced (~1 cm) on an endocardial lead, then there is little interference from cautery as long as it is not directly over the sensing electrode pair. By contrast, when sensing of the heart electrical activity by endocardial leads is from a more widely spaced bipole pair of electrodes, for example, from the tip electrode of the right ventricular pacing lead to the defibrillation coil electrode about 4 cm away, then the larger distance between the bipole sensing electrodes increases the sensitivity to unwanted far field signal including electrical activity coming from outside the heart, such as electro-cautery.

As just described, when electric cautery is applied to the upper chest region during implantation or extraction of a pulse generator, or during any surgery requiring such cauterization, interfering signals may result in the device. The cautery instrument generates electricity that is powerful enough to burn tissue and is therefore much stronger than the weak electrocardiographic signals produced by the heart. The circuits in the pulse generator that monitor these cardiac signals are consequently designed with filtering to reject the cautery noise. However, filtering is usually insufficient due to the large relative power of the cauterization energy, so that interference still occurs.

To understand the important variables of interference, consider that the cautery instrument produces an electric field in body that is created from the cauterization electrodes. The geometric relationship between the cautery electrode pair and the monitoring electrode pair of the pulse generator determine the magnitude of the interference.

The closer the monitoring electrodes from the pacemaker or defibrillator are to the cautery ones, the greater the interference. This is because the voltage produced by a cautery dipole decays as the inverse of the distance from it (1/r).

Similarly, the distance between the monitoring electrodes themselves is also an important variable, with wider spaced electrodes yielding larger voltages, as can be readily observed in any biopotential recording. A larger spaced monitoring pair (such as the pacing lead tip to coil in the ICD case) will traverse a greater potential gradient in any electric field that exists in the thoracic tissues and inherently result in the generation of a larger detected signal than will a closely spaced electrode pair (such as the bipolar sensing electrode on the ICD pace-sense lead).

Other variables of relevance are the surface area of the 4 electrodes involved (i.e., 2 on the device lead in the heart, and 2 on the electro-cautery instrument) and the relative orientation between the electric field and the monitoring electrodes. For example, a larger surface electrode will lead to greater voltages, as will a perpendicular orientation of the monitoring pair relative to the local isopotential lines of the cautery electric field.

Radio frequency (RF) interference can also be caused by electromagnetic radiation, where the effects are transmitted and received by antennae formed by the cautery and implanted lead conductors. However, transmission of these RF signals through body fluids is much smaller in comparison to the field set up in the tissues by direct electrode application.

From the above considerations, it can be appreciated that a monitoring electrode pair that has a short inter-electrode distance—such as a true or dedicated bipolar configuration—will have better noise rejection than one with a larger inter-electrode distance, such as an "integrated bipolar" (e.g., small tip electrode to a larger more proximal electrode such as an ICD coil electrode with an effective inter-electrode distance usually >2 cm) or a "unipolar configuration." (i.e., from small tip electrode to 'can' or 'shield' of an implanted device with an effective inter-electrode distance typically >8-10 cm) or a "unipolar configuration." Furthermore, using smaller surface areas in the monitoring electrodes, as in "true bipole" configurations, provides further reduction of the interfering signal over that of an "extended bipole" configuration (i.e., either 'integrated bipole', unipolar configuration, or the like), and yields monitoring that is focused on the local cardiac tissue. These advantages appear by virtue of the same mechanisms present in the use of bipolar configurations when rejection of far field signals is desired, as is well known in the practice of electrophysiology. In some circumstances when electro-cautery is performed within 1-2 cm of the dedicated bipolar sensing electrodes, cautery may theoretically still be incorrectly sensed by the ICD as ventricular fibrillation. Thus, there may be a small part of the body, within 1-2 cm of the dedicated bipolar electrode pair, that is not cautery-safe. As such, in the case of an embodiment when dedicated bipolar ventricular lead is positioned in the ventricular apex, theoretically electro-cautery within 1-2 cm of the left nipple directly above the right ventricular apex, may still be incorrectly sensed by the ICD as ventricular fibrillation and pacing could be inhibited.

Referring now to FIG. 1, one embodiment of an implantable electronic device, such as a pulse generator 190, will be described. Pulse generator 190 is constructed of a header 100 and an hermetic housing 180 which houses the electronics employed to operate the device. Housing 180 is typically constructed of a metallic housing, often referred to as the "can." Header 100 is typically a plastic component that includes ports for connecting the leads coupled to the heart, Coupled to header 100 is a right ventricular lead 120 that separates into three connectors 110. Lead 120 comprises electrical wires or conductors that transmit electrical current between device 190 and various electrodes at the other end of lead 120.

In this example, three connectors 110 are included. However, it will be appreciated that a lead may have a variety of connectors, ranging from 1 to 4 or more. Lead 120 contains four electrodes: a proximal defibrillation coil 130, a distal defibrillation coil 140, a ring electrode 150 and a tip electrode 160. Lead 120 is shown entering into the right ventricular apex of the heart 170, with the right side of the heart cut away for convenience of illustration. Although not shown in FIG. 1, additional leads besides the right ventricle ones may connect device 190 to the heart. For example, there could be a right atrium lead, and a left ventricle lead. If present, these leads typically have their corresponding connecting ports in header 100.

Figure 2A:
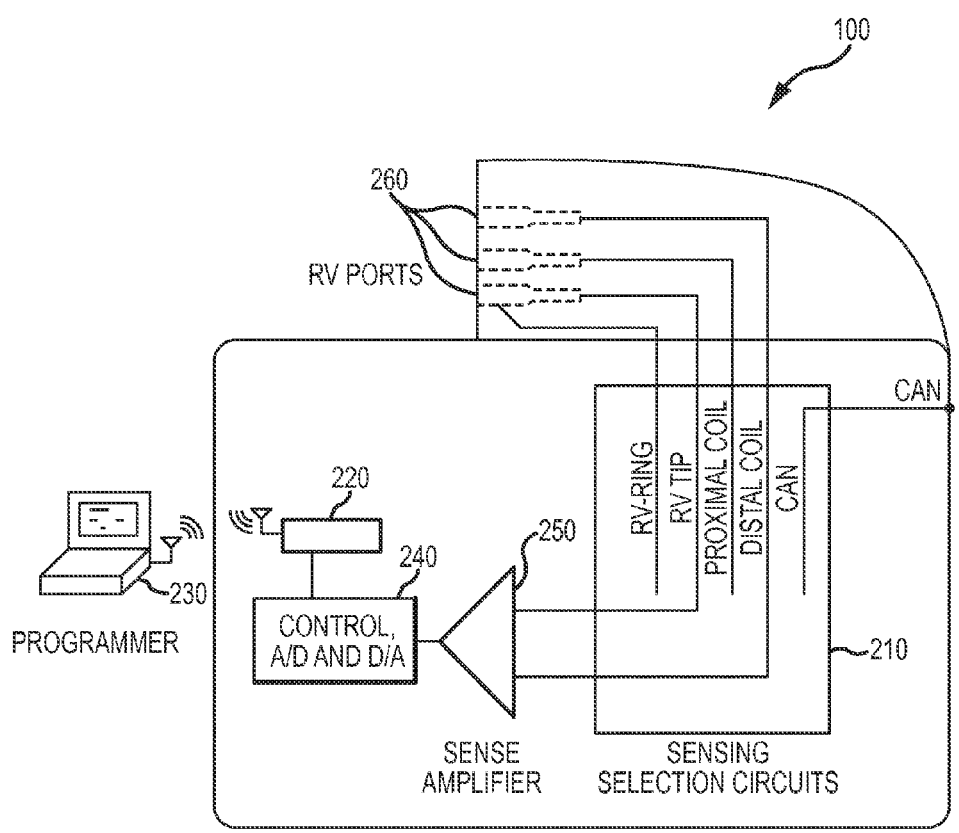
FIG. 2A illustrates a schematic view of the implantable device of FIG. 1 being in an integrated bipolar sensing mode.

FIGS. 2A-2D illustrate schematic views of the device 190 shown in FIG. 1. FIG. 2A illustrates a schematic view of device 190 of FIG. 1. As shown, implantable device 190 is in an integrated bipolar sensing mode, which is one operating scenario for the implantable device. The implantable device includes various sensing selection circuits 210 used to switch the connectors between the various sensing configurations known in the art. For example, switches are provided to switch between the RV ring electrode, the RV tip electrode, the proximal coil, the distal coil, and the can. Switching may be accomplished using various types of transistors, such as but not limited to a field-effect transistor switch. Implantable device 190 also includes a wireless transceiver 220 that may receive wireless signals from a programmer 230. These signals are transmitted to a unit 240 that may contain a processor controller, and various analog to digital or digital to analog converters. A sense amplifier 250 may amplify the signal selected by the sensing selection circuits 210. The sense amplifier may also provide detection circuits to determine the presence and timing of cardiac events. Header 100 includes various ports 260 into which the various connectors of leads are coupled. Here only the right ventricle (RV) ports are shown, although header 100 could have ports for other leads such as a right atrial lead, and/or a left ventricle lead, and the like.

In FIG. 2A, the device is shown in an integrated bipolar sensing mode. In this case, the RV tip electrode and the distal coil electrodes are actively coupled to the sense amplifier 250. Because of the relatively long distance between the tip electrode 160 and the distal coil 140 as shown in FIG. 1, use of cautery during a procedure may interfere with operation of the implantable device (i.e., longer electrode spacing within the generated electrical fields as discussed earlier). The circuit shown in FIG. 2A wherein the tip electrode 160 and distal coil electrode 140 are actively coupled together is programmed to one potential "integrated bipolar" sensing configuration.

Figure 2B:
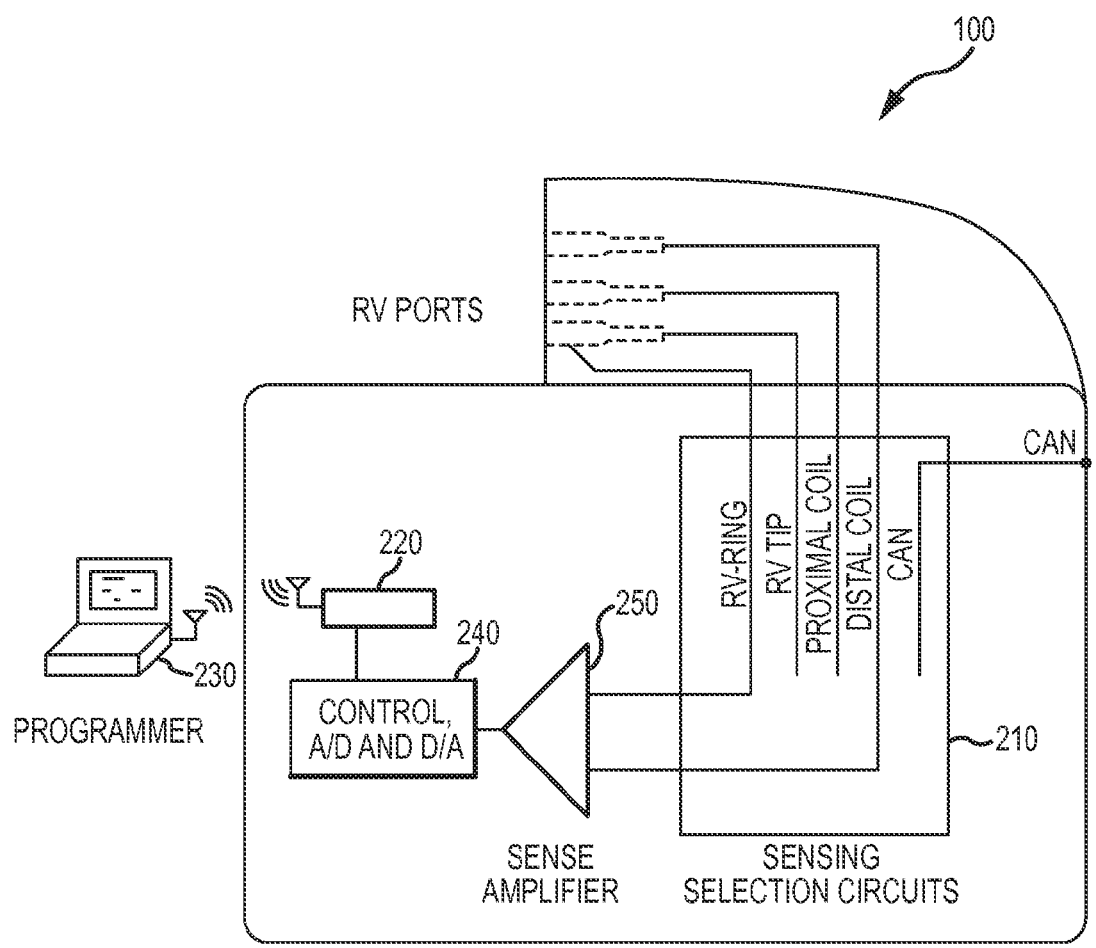
FIG. 2B illustrates a schematic view of the implantable device of FIG. 1 in an alternative integrated bipolar sensing mode.

FIG. 2B illustrates the device of FIG. 2A that is placed into an alternative integrated bipolar sensing configuration. In this configuration, the sensing election circuits 210 are arranged such that the RV ring electrode (150 in FIG. 1) and the distal coil electrode (140 in FIG. 1) are coupled to the sense amplifier 250. Similar to the arrangement in FIG. 2A, the two selected electrodes that are actively coupled together for sensing are sufficiently spaced so that cauterization may interfere with operation of the implantable device.

Figure 2C:
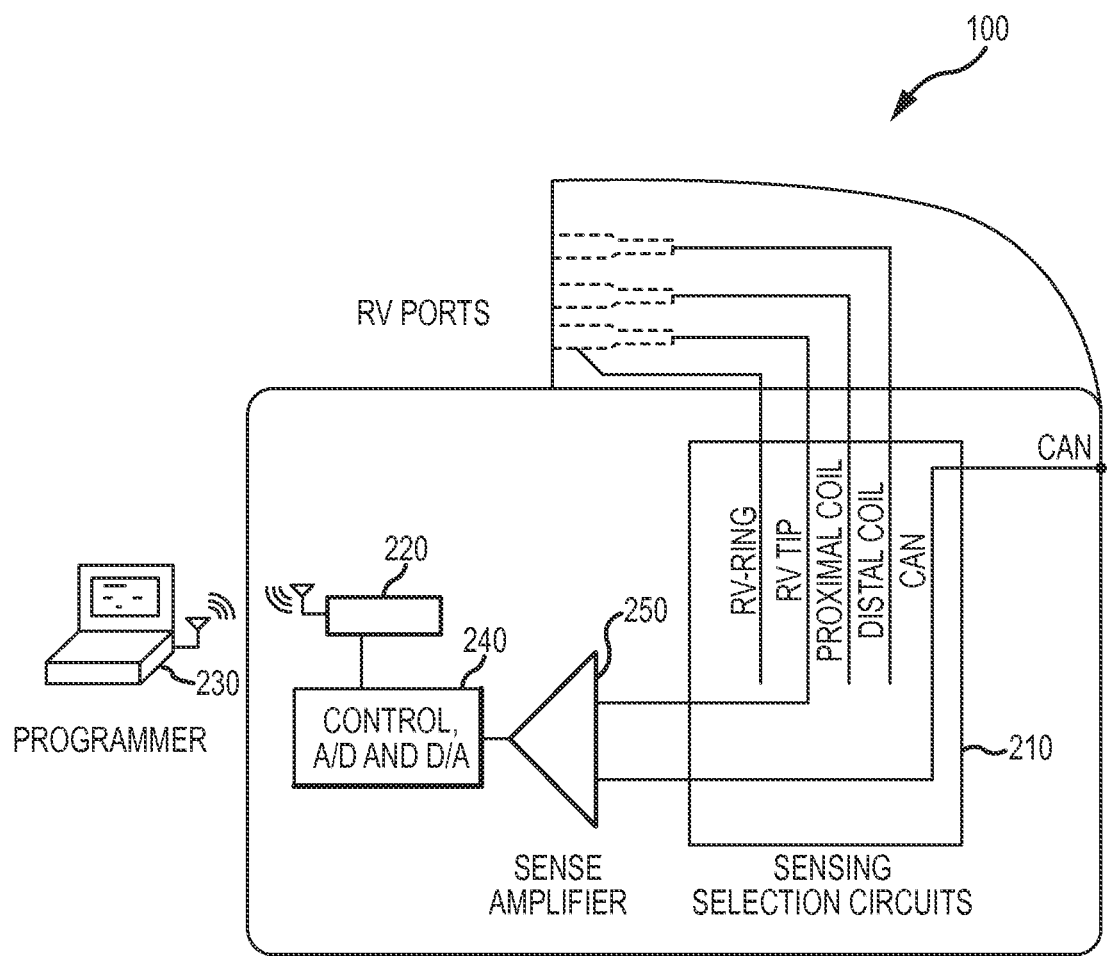
FIG. 2C illustrates a schematic view of the implantable device of FIG. 1 in a unipolar configuration.

In FIG. 2C, the device is placed into a unipolar configuration where the RV tip electrode (160 in FIG. 1) and the electrically active pulse generator can (180 in FIG. 1) as the second electrode are actively coupled to the sense amplifier 250. As with the arrangements in FIGS. 2A and 2B, this configuration also presents problems during cauterization due to the larger (effectively longer) inter-electrode spacing.

Figure 2D:
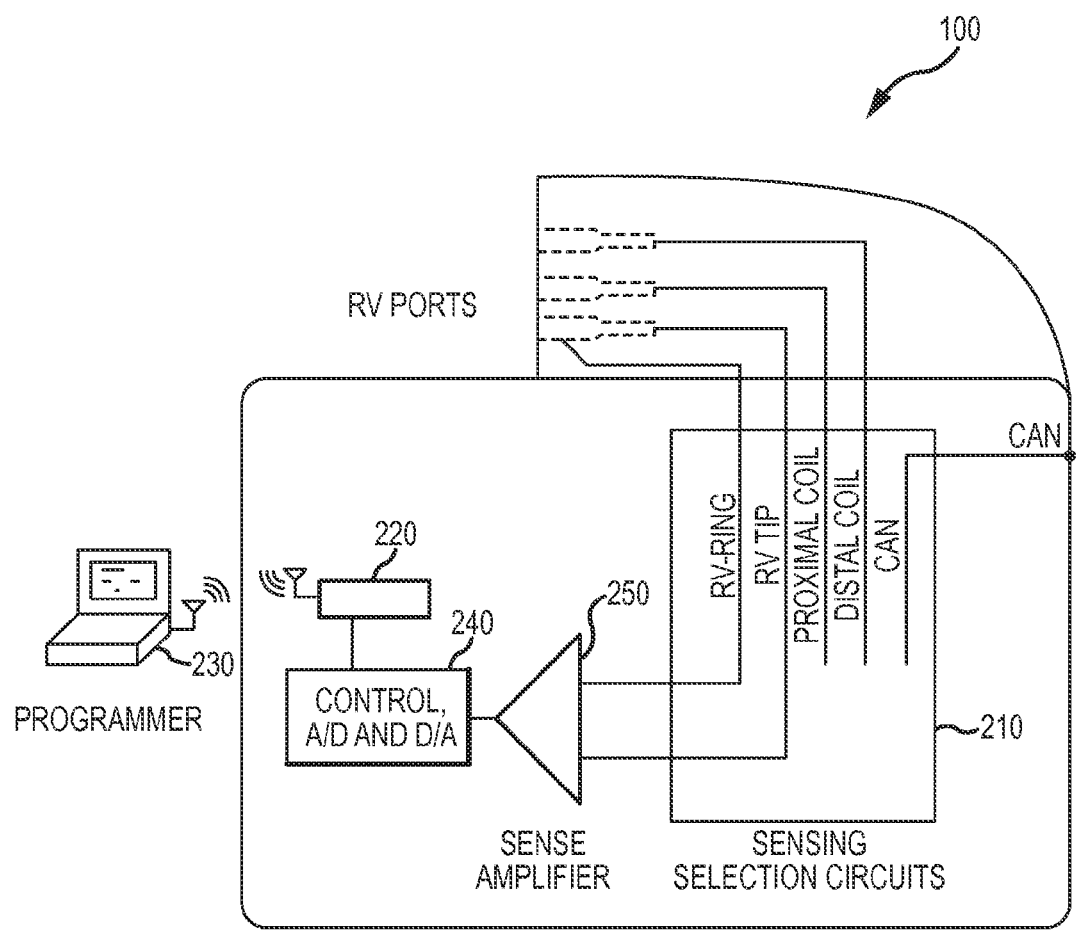
FIG. 2D illustrates a schematic view of the implantable device of FIG. 1 in a true bipolar or dedicated bipolar configuration according the invention.

In FIG. 2D, programmer 230 has been employed to switch circuits 210 to a true bipolar (also known as dedicated bipolar) configuration as described herein. In this case, the ring electrode (150 in FIG. 1) and tip electrode (160 in FIG. 1) are actively coupled to the sense amplifier 250. Because these distal electrodes are so close to each other, use of cauterization will not interfere with the sensing or therapeutic modalities of the implantable device. As such, one important aspect of the invention is the ability to switch implantable device 190 to the electrode configuration illustrated in FIG. 2D so that use of cauterization during a procedure will not interfere with operation of the implantable device. It is possible for some commercial systems to be switched permanently into the configuration of FIG. 2D and that configuration may be the preferred mode of sensing. In such cases, this true bipolar sensing mode may be renamed as the cautery-safe mode and the invention may allow for programming of this cautery-safe mode. Further, in some embodiments the invention provides a way to program into and out of the cautery-safe mode more easily, for example, with a hand held device, and with the capability of a timed reversion to a normal mode. As described hereinafter, programmer 250 may be employed to place the implantable device into a cautery-safe mode, which is the circuit illustrated in FIG. 2D. Hence, if the implantable device is operating in any of the normal configurations illustrated in FIGS. 2A through 2C, the instructions from the programmer may cause the selection circuits to switch to the configuration shown in FIG. 2D where the device is placed into the cautery-safe mode. Further, the instructions from programmer 230 may include a time limit, after which the sensing selection circuits 210 will automatically revert back to their prior permanent operating modes as shown in FIGS. 2A through 2C. This may be, for example, one to two days (or even longer) after placing the electrode pair into the dedicated bipolar configuration. FIGS. 1 and 2A-2D are meant to be illustrative of one of multiple possible pulse generator, lead, and circuit configurations and thus not meant to be limiting.

Figure 3:
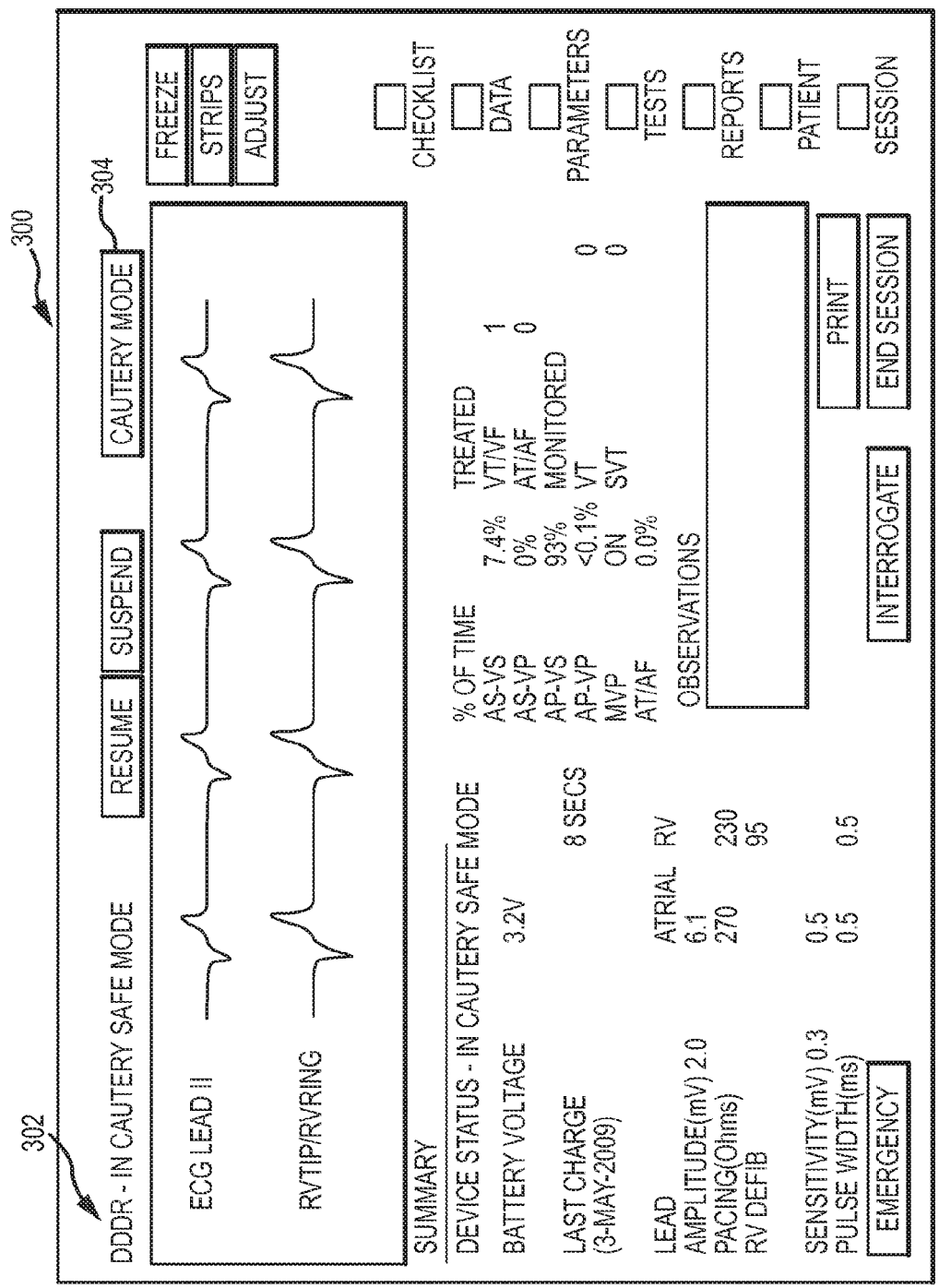
FIG. 3 illustrates a screen display illustrating a user interface of a programmer that may be employed to program an implantable device into a cautery-safe mode according to the invention.

FIG. 3 illustrates one example of a display screen 300 that may be shown on a programmer and used to place an implantable device into a cautery-safe mode. Display screen 300 has text 302 for displaying the pacing mode of the device, in this example, it is DDDR. As shown, the implantable device is now in a cautery-safe mode (such as in the configuration shown in FIG. 2D). The display screen also illustrates various electrogram wave forms that are being sensed and monitored by the device. In this example the true bipolar sensing electrograms are illustrated as sensing is from the RV tip to RV ring electrodes. Various control buttons and other panels with information on the status of the device are also illustrated. A cautery-safe mode button 304 is highlighted on the display screen and may be selected by a pointing device, such as a mouse, or "touch screen" wand, or even by the operator's finger, to place the implantable device into the cautery-safe mode. Although not shown, once cautery mode 304 is selected, another display screen may be provided to permit the user to specify the time that the cautery-safe mode should remain in place.

Figure 4:
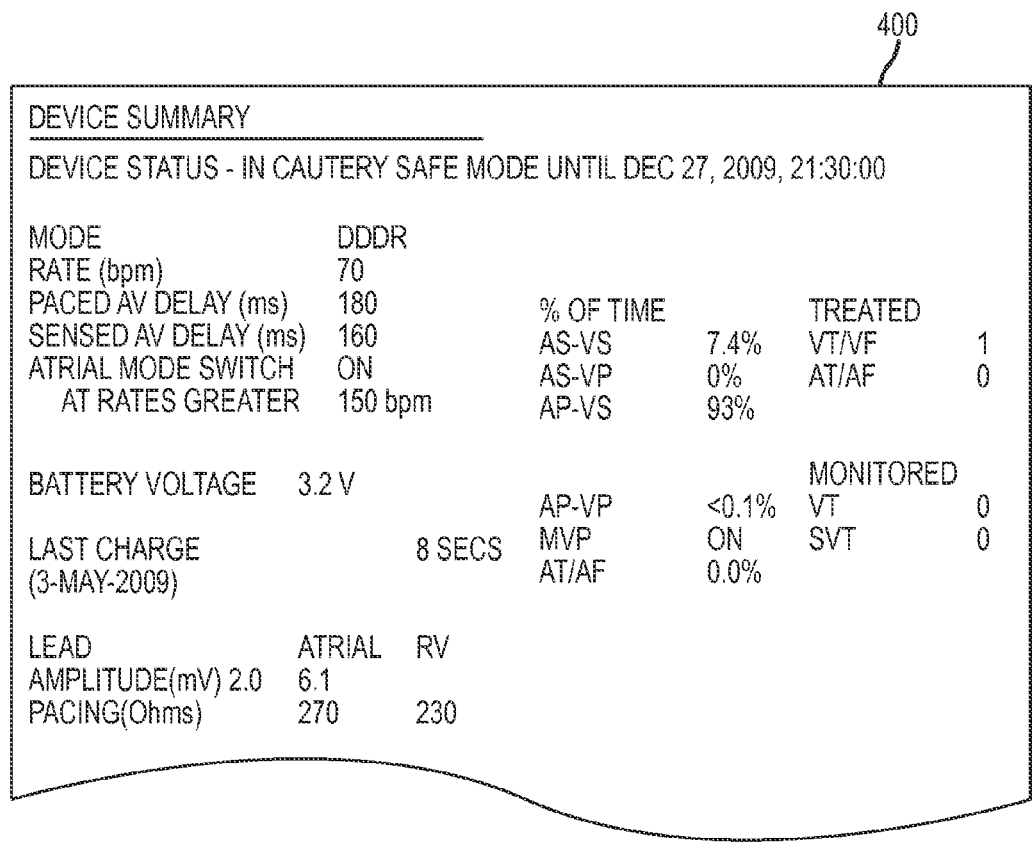
FIG. 4 illustrates a report that may be printed after programming an implantable device into a cautery-safe mode according to the invention.

FIG. 4 illustrates one embodiment of a paper report 400 that may be printed by a printer that is coupled to a programming device (or programmer) after the implantable device has been placed in the cautery-safe mode. Report 400 includes various pieces of information such as the device status which indicates that the implantable device is in a cautery-safe mode and gives a date upon which the implantable device will return to its prior operating mode. This report, which could be printed or transmitted to an electronic medical record, may be taken to the operating room during the day of surgery to provide documentation that the implantable device has already been placed in the cautery-safe mode so that the caregivers will know that it is safe to use cautery with the procedure without interfering with the operation of the implantable device.

Figure 5:
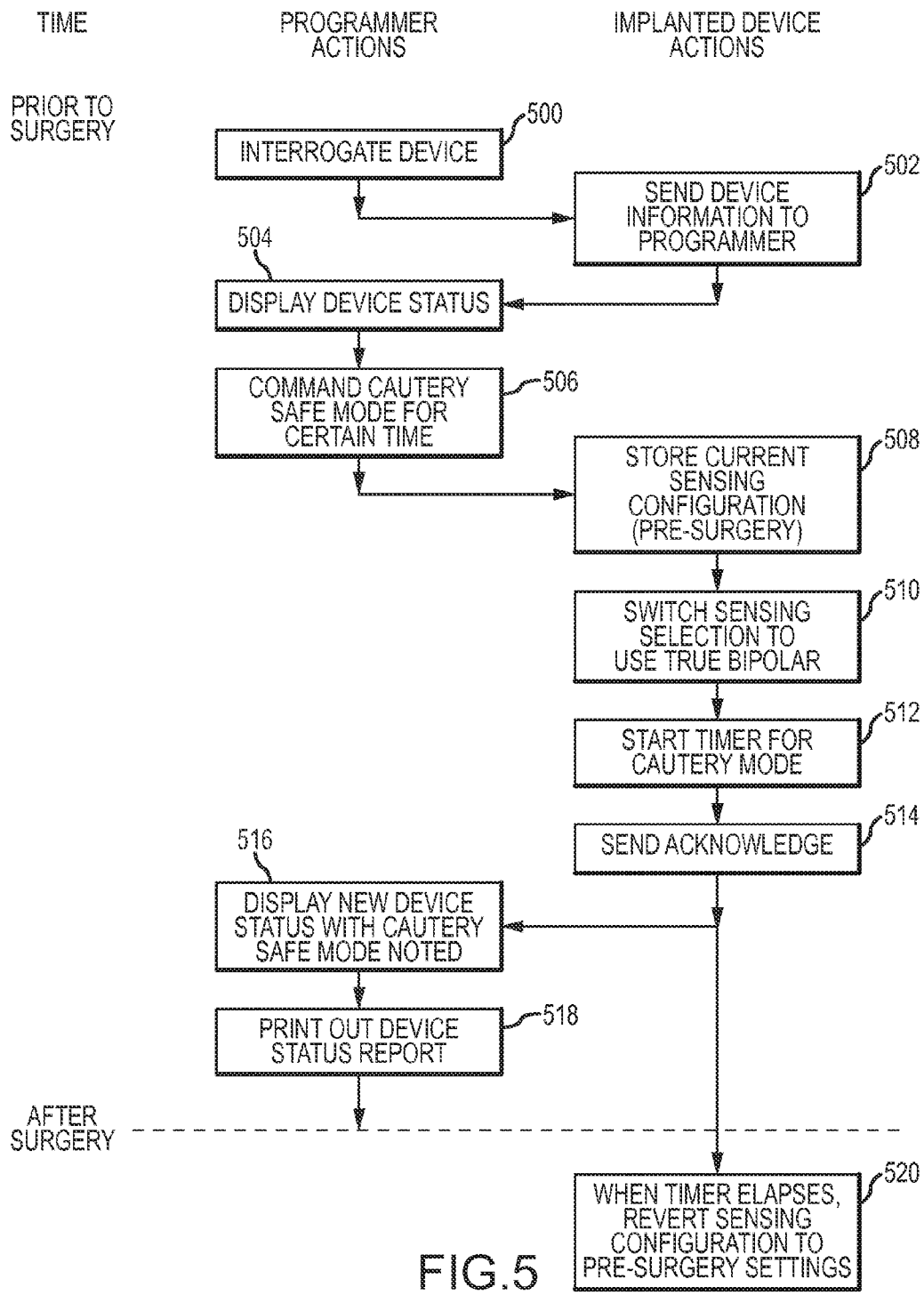
FIG. 5 is a flowchart illustrating one embodiment of a method for programming an implanted device into a cautery-safe mode according to the invention.

Referring now to FIG. 5, one exemplary method for placing an implantable device into a cautery-safe mode will be described. In FIG. 5, the chart is divided into time in the left hand column and the actions taken by the programmer and the implanted device in the next two columns. As illustrated in step 500, prior to a surgery the implantable device is interrogated to determine the status of the device. This is accomplished by sending a wireless signal from the programmer to the implantable device. In step 502, the implanted device sends a wireless signal back to the programmer with information indicating the status of the device. In step 504, the status of the implantable device is displayed on a display screen of the programmer computer. At this point, the caregiver may decide to place the implantable device into a cautery-safe mode for a certain time. This is illustrated in step 506. To do so, the caregiver may select an icon or button on the display screen of the programmer. In turn, this transmits a wireless signal to the implantable device. Additional confirmatory steps could also be included in this programming sequence. As such, FIG. 5 is meant only to be illustrative and not limiting. At step 508, the implantable device stores the current sensing configuration, meaning the configuration of the implanted device prior to being reprogrammed to the cautery-safe mode. In step 510, the implanted device switches its sensing selection to a true bipolar configuration similar to that shown in FIG. 2D. Also, as illustrated in step 512, a timer is started for the cautery-safe mode. An acknowledgement is also transmitted back in step 514 to the programmer to confirm that the implanted device has been reprogrammed to the cautery-safe mode. As illustrated in step 516, this may be displayed on the display screen of the programmer. Also, a device status report may be printed out so that the reprogramming may be documented and provided on the day of surgery. Finally, following surgery and after the timer has elapsed, the sensing configuration is returned to the presurgery settings as illustrated in step 520. In some cases there may not be a timer, as shown in step 512. In some cases the sensing circuitry may already be programmed to the true dedicated bipolar mode in which case no switching into a cautery-safe mode is needed but step 514 would still provide confirmation that the implanted device is in a cautery-safe mode.

While method illustrated in FIG. 5 is primarily useful for a programmer having a display screen, some of the steps could also be used with a simplified handheld device that does not include a display screen or uses a small screen such as is commonly used on "smart phones". In some cases a "smart phone", such as an Apple iPhone could have an application to enable it to become the handheld device. In such cases, steps such as displaying the device status, the reprogrammed device status and printing would not be needed. Also, although not shown various additional steps could be provided following surgery. For example, a nurse could interrogate the device prior to patient discharge from the surgical recovery unit or hospital and the results could be printed or transmitted and stored electronically along with post surgery conditions. In addition, such a handheld device, like a "smart phone" may have additional applications making it possible to identify the implanted device and program it to different pacing configurations, for example, from the VVI pacing mode wherein the ventricle is sensed, paced, and pacing is inhibited if the device senses an intrinsic heart beat to the VVO mode wherein the ventricle is paced continuously and sensing is inhibited.

The invention has now been described in detail for purposes of clarity and understanding. However, it will be appreciated that the figures have been provided to illustrate the inventions but additional lead configurations, circuit configurations, lead designs, pulse generator designs, and programmer designs have not been described but will also allow for practice of the proposed art. Thus, certain changes and modifications may be practiced within the scope of the appended claims.

What is claimed is:

1. A method for programming an implantable pulse generator (IPG) in a patient, the method comprising:
    showing on a display screen of a computer having a processor a display giving a user the option of programming the IPG to a cautery-safe mode;
    receiving an input at the computer to place the IPG in the cautery-safe mode;
    transmitting a signal from the computer to the IPG reprogramming the IPG from a non-cautery-safe mode to the cautery-safe mode, wherein electrode configuration settings of the IPG are modified upon reprogramming so that sensing electrodes of the IPG that are chosen to be spaced less than 10 mm from each other are activated, and so that operation of the IPG is unaffected by electrical noise produced by an electro-cautery device when operating.

2. A method as in claim 1, wherein the sensing electrodes are in a dedicated bipolar sensing configuration which may be displayed upon interrogation or analysis of the IPG when the IPG is in cautery-safe mode.

3. A method as in claim 1, wherein the IPG is a device selected from one of a cardiac pacemaker and an implantable cardioverter defibrillator.

4. A method as in claim 1, further comprising displaying on the display screen a confirmation that the IPG is in the cautery-safe mode.

5. A method as in claim 1, further comprising printing, using a printer coupled with the computer, a confirmation that the IPG is in the cautery-safe mode.

6. A method as in claim 1, further comprising receiving an entry indicating a time to return the IPG to the non-cautery-safe mode.

7. A method as in claim 1, wherein the non-cautery-safe mode is a mode where the sensing electrodes are in an integrated bipolar sensing configuration.

8. A method as in claim 1, further comprising modifying therapeutic settings of the IPG upon reprogramming the IPG from the non-cautery-safe mode to the cautery-safe mode.

9. A method as in claim 1, further comprising maintaining therapeutic settings of the IPG upon reprogramming the IPG from the non-cautery-safe mode to the cautery-safe mode.

10. A method as in claim 1, further comprising reprogramming the IPG from the non-cautery-safe mode to the cautery-safe mode on a day prior a scheduled surgery or procedure.

* * * * *